United States Patent
McDonald et al.

(10) Patent No.: US 8,507,516 B2
(45) Date of Patent: *Aug. 13, 2013

(54) AZABICYCLIC COMPOUNDS AS ALPHA-7 NICOTINIC ACETYLCHOLINE RECEPTOR LIGANDS

(75) Inventors: Ivar M. McDonald, East Haddam, CT (US); Robert A. Mate, Waterbury, CT (US); James H. Cook, II, East Hampton, CT (US); Dalton King, Hamden, CT (US); Richard E. Olson, Orange, CT (US); Nenghui Wang, Guilford, CT (US); Christiana I. Iwuagwu, Hamden, CT (US); F. Christopher Zusi, Hamden, CT (US); John E. Macor, Guilford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 198 days.

This patent is subject to a terminal disclaimer.

(21) Appl. No.: 12/911,882

(22) Filed: Oct. 26, 2010

(65) Prior Publication Data

US 2011/0269787 A1   Nov. 3, 2011

Related U.S. Application Data

(60) Provisional application No. 61/255,794, filed on Oct. 28, 2009.

(51) Int. Cl.
- *C07D 401/04* (2006.01)
- *A61K 31/438* (2006.01)
- *A61K 31/439* (2006.01)

(52) U.S. Cl.
USPC .......................................... 514/278; 546/18

(58) Field of Classification Search
USPC ............................................ 546/18; 514/278
See application file for complete search history.

(56) References Cited

U.S. PATENT DOCUMENTS

| | | |
|---|---|---|
| 5,053,412 A | 10/1991 | Fisher et al. |
| 7,863,291 B2 | 1/2011 | Cook, II et al. |
| 2007/0004715 A1 | 1/2007 | Huang et al. |
| 2010/0099684 A1 | 4/2010 | Cook, II et al. |

FOREIGN PATENT DOCUMENTS

| | | |
|---|---|---|
| EP | 0 337 547 | 10/1989 |
| EP | 0 452 101 | 10/1991 |
| WO | WO 96/06098 | 2/1996 |
| WO | WO 03/092580 | 11/2003 |
| WO | WO 2005/005435 | 1/2005 |
| WO | WO 2006/065209 | 6/2006 |
| WO | WO 2008/000469 | 1/2008 |

OTHER PUBLICATIONS

U.S. Appl. No. 12/907,122, filed Oct. 19, 2010, McDonald et al.
U.S. Appl. No. 13/097,153, filed Apr. 29, 2011, Lentz et al.
Swain, C.J. et al., "Novel 5-$HT_3$ Antagonists: Indol-3-ylspiro(azabicycloalkane-3,5'(4'H)-oxazoles)", Journal of Medicinal Chemistry, vol. 35, No. 6, pp. 1019-1031 (1992).
Tatsumi, R. et al., "(R)-3'-(3-Methylbenzo[b]thiophen-5-yl)spiro[1-azabicyclo[2,2,2]octane-3,5'-oxazolidin]-2'-one, a Novel and Potent α7 Nicotinic Acetylcholine Receptor Partial Agonist Displays Cognitive Enhancing Properties", Journal of Medicinal Chemistry, vol. 49, No. 14, pp. 4374-4383 (2006).

*Primary Examiner* — Rita Desai
(74) *Attorney, Agent, or Firm* — James Epperson

(57) ABSTRACT

The disclosure provides compounds of formula I, including their salts, as well as compositions and methods of using the compounds. The compounds are ligands for the nicotinic α7 receptor and may be useful for the treatment of various disorders of the central nervous system, especially affective and neurodegenerative disorders.

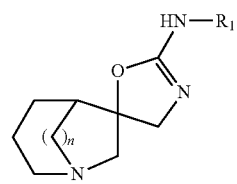

3 Claims, No Drawings

AZABICYCLIC COMPOUNDS AS ALPHA-7 NICOTINIC ACETYLCHOLINE RECEPTOR LIGANDS

CROSS REFERENCE TO RELATED APPLICATIONS

This patent application claims the benefit of U.S. provisional patent application No. 61/255,794 filed Oct. 28, 2009.

BACKGROUND OF THE INVENTION

The disclosure generally relates to compounds of formula I, including their salts, as well as compositions and methods of using the compounds. The compounds are ligands, agonists and partial agonists for the nicotinic α7 receptor and may be useful for the treatment of various disorders of the central nervous system, especially affective and neurodegenerative disorders.

Schizophrenia is a serious mental disorder, affecting approximately 1% of the population. Its progressive course results in major impairment of mental and social functioning and often leads to the development of other pathologies. Susceptibility often runs in families, with both genetic and environmental factors thought to be important. The direct and indirect costs of the disease are estimated in the tens of billion dollars annually in the U.S. alone.

Patients with schizophrenia have an elevated risk of suicide (approximately a 10% lifetime risk). They have a 2.5 fold increase in all-cause mortality, resulting in a 20% lowered life expectancy. The onset of illness can result in cascade of unhealthy lifestyle factors and behaviors that elevate the risk of various conditions and consequently the risk of death.

The onset of schizophrenia is most often in late adolescence or early adulthood, and episodes recur throughout life. The disease is characterized by the expression of three distinct symptom domains: positive, negative and cognitive. Psychotic or positive symptoms include delusions, hallucinations, thought disorder and paranoia. Negative symptoms include negative affect, social withdrawal, and anhedonia. Cognitive dysfunction includes deficits in attention, working memory and executive function. The pathophysiology of schizophrenia is not well understood, however, most experts believe it is a multi-factorial disorder in which biological, genetic and environmental factors play a role. Most current therapies target the dopaminergic system and have resulted in the suggestion that an excess of dopaminergic neurotransmission underlies at least some aspects of schizophrenia. This theory received further support from findings that drugs which increase the levels of dopamine cause psychoses similar to the positive symptoms of the disease. Also, post mortem analysis of brains from schizophrenic patients indicate increased numbers of D2 dopamine receptors. Although newer antipsychotic agents, known as atypical antipsychotics, which are active at several additional neurotransmitter receptors, have been introduced in the past decade, these agents still share efficacy against the D2 dopamine receptor. All currently-used agents also have major limitations. Although positive symptoms are generally reduced in a majority of patients, these drugs do little to relieve the negative symptoms and cognitive deficits that are common and often most debilitating. In addition, antipsychotic agents have a number of unwanted and limiting side effects.

Nicotine is among the few agents which have a positive effect on cognitive function. Many schizophrenics smoke; the rate in patients is 2-4 times that of the general population, and up to 90% in schizophrenics who have been institutionalized do smoke. This smoking habit has been characterized as a form of self-medication.

Nicotinic acetylcholine receptors (nAChR's) are pentameric ligand-gated ion channels which are widely expressed through the central and peripheral nervous system. These channels are fast-desensitizing calcium channels which, when open, increase the intracellular concentration of the $Ca^{++}$ ion. Although there are 12 individual receptors, the most abundant nicotinic receptors in the brain are α4β2 and α7. The α4β2 complex has been identified as the "high affinity" nicotine site. The homo-pentameric α7 receptor selectively binds the natural product, α-bungarotoxin, which has allowed its relatively facile localization and measurement. The α7 receptor is primarily expressed in the cortex, hippocampus and subcortical limbic regions and commonly occurs presynaptically. The localization of α7 nAChRs in areas involved with learning and memory has led to studies using both knockout mice and pharmacological manipulation. It is involved in sensory gating, memory, and neuronal plasticity. Alpha7 agonists have been shown to increase the release of neurotransmitters in rodents, including dopamine, serotonin, glutamate and GABA. Compounds which selectively bind to the α7 receptor, such as α7 agonists and partial agonists, have been shown to improve learning and memory functions in normal and aged animals, reverse scopolamine-induced memory deficits, reverse deficits in cognition induced by NMDA antagonists, reverse pharmacologically-induced gating deficits, e.g. amphetamine induced gating disruption, and to possess some anxiolytic properties. The α7 agonists of the present invention are expected to be useful in the treatment of schizophrenia and cognitive disorders associated with schizophrenia.

Alzheimer's disease is a progressive neurodegenerative disorder, resulting in the general loss of cognitive functions. The incidence increases with age, to the degree that 25-50% of all individuals over 85 are estimated to suffer from some degree of dementia. A diagnosis of Alzheimer's implies that the remaining life expectancy is reduced by half, compared to normal adults.

Clinical signs of Alzheimer's disease are progressive cognitive deterioration, decreased ability to perform the activities of daily living and neuropsychiatric symptoms or behavioral changes. In the advanced stages of the disease, deterioration of musculature and mobility may lead to inability to feed oneself, and eventually to the patient becoming bedridden. Language becomes severely disorganized, and then is lost altogether. Patients are not able to perform even simple tasks independently and require constant supervision. The cost of institutional care makes up nearly 70% of the cost of the disease. Therefore, therapies which increase cognitive function and delay institutionalization are greatly needed.

Alzheimer's disease has been shown in several studies to be accompanied by a reduction in nicotinic receptors in the cortex and hippocampus. Nicotine injections or nicotine skin patches have been reported to significantly improve attention, memory and learning in Alzheimer's disease patients. While there is a progressive loss of nicotinic receptors during the course of Alzheimer's disease, the α7 neurons are relatively spared, compared to the more abundant α4 receptors. Recently, the administration of selective nicotinic α7 agonists has been shown to increase cognitive functioning in Alzheimer's patients when dosed as long as 8 weeks. This clinical data is consistent with pre-clinical data showing α7 agonists and partial agonists improve learning and memory functions in normal and aged animals and reverse scopolamine-induced memory deficits. Thus, the compounds of the present invention may be useful in the treatment and prevention of Alzheimer's disease. The amyloid peptide Aβ42 has been shown to bind to the α7 nicotinic receptor (Wang et al., J. Biol. Chem., 2000, 275:5626-5632; J. Neurochem. 2000, 75:1155-1161). This association may facilitate the aggregation of Aβ42, believed to be important in the toxic effects of Aβ42, and may also cause disregulation of signaling through α7 nicotinic receptors. Deletion of the a7 receptor gene improves cognitive deficits and synaptic pathology in a mouse model of Alzheimer's disease (Dziewczapolski et al., J. Neuroscience, 2009, pp 8805-8815). The compounds of the present invention may disrupt the interaction of Aβ42 and α7 receptors. Treatment with α7 agonists and partial agonists may represent an approach for disease modification in Alzheimer's disease. Alpha7 receptors may also mediate inflammatory processes in neurodegenerative conditions, such as Alzheimer's disease (Conejero-Goldberg et al., Neurosci. and Biobehav. Rev., 2008, 32, pp 693-706). The α7 agonists and partial agonists of the present invention may be useful in reducing inflammation in neurodegenerative diseases and disorders, such as Alzheimer's disease.

The α7 receptor has also been shown to be involved in the reduction of inflammation via the vagus nerve. In addition, the α7 receptor is expressed in synoviocytes from RA and OA patients, and α7 agonists have been shown to inhibit the proinflammatory cascade that occurs in the rheumatoid joint (Waldberger et al., Arthritis and Rheumatism, Vol 58, pp 3439-3449). Thus, the compounds of the present invention may be useful in the treatment of inflammatory conditions, such as rheumatoid arthritis and osteoarthritis.

Nicotinic receptors containing the α7 subunit are present on mucosal mast cells known to be involved in gastrointestinal hypersensitivity (Kageyama-Yahara et al., Biochem and Biophys. Research Commun., 2008, v. 377, pp 321-325). The α7 agonist GTS-21 inhibits the antigen-induced degranulation of mucosal mast cells, suggesting that α7 agonists may be useful in the treatment of hypersensitive bowel conditions, such as ulcerative colitis.

In a recent report (Marrero et al., JPET Fast Forward, Sep. 28, 2009, DOI: 10.1124/jpet.109.154633), an α7 agonist was shown to decrease weight gain and food intake and reduce the elevated plasma levels of triglycerides, glucose, glycated hemoglobin and TNFa in a mouse model of type II diabetes (db/db mice which are deficient in leptin receptors). The α7 agonists and partial agonists of the present invention may be useful in the treatment of diabetes.

The following references provide general reviews of the nicotinic receptor system and α7 receptors and ligands: Picciotto and Zoli, J. Neurobio. (2002) 53:641-655; Brening, et al, Ann. Reports in Med. Chem. (2005) 40:3-16; Dani and Bertrand, Ann. Rev. Pharm. Tox. (2007) 47:699-729; Olincy and Stevens, Biochem. Pharmacol. (2007) 74:1192-1201; Broad, et al, Drugs Future (2007) 32 (2):161-70; de Jonge and Ulloa, Brit. J. Pharmacal. (2007) 151:915-929; Romanelli, et al, Chem Med Chem (2007) 2(6):746-767; Lightfoot et al., Progress in Medicinal Chemistry (2008), v 46, pp 131-171; Concotta et al., Current Opinion in Investigational Drugs (2008), v 9, pp 47-56; Leiser et al., Pharmacal. and Therapeutics (2009), doi:10:1016/j.pharmthera.2009.03.009).

Ligands for the nicotinic α7 receptor have been disclosed in the references above, and also in US patent application publication U.S. 20090270405, U.S. 2007004715, WO 2008/000469, WO 2003/092580, WO 2004/000,469, EP 337,547, EP 452,101, and C. J. Swain, et al., J. Med. Chem., (1992) 35:1019-1031.

The invention provides technical advantages, for example, the compounds are novel and are ligands for the nicotinic α7 receptor and may be useful for the treatment of various disorders of the central nervous system, especially affective and neurodegenerative disorders. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds formula I, including pharmaceutically acceptable salts, and compositions and methods of treatment using these compounds. The compounds may be useful for the treatment of various disorders of the central nervous system:

One aspect of the invention is a compound of formula I, or a stereoisomer thereof,

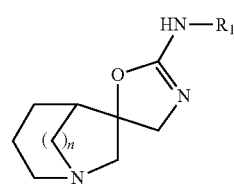

wherein:

$R^1$ is selected from the group consisting of isoxazolyl, pyrazolyl, oxazolyl, thiazolyl, imidazolyl, oxadiazolyl, thiadiazolyl, triazolyl, pyridinyl, pyrazinyl, pyridazinyl, pyrimidinyl, triazinyl, quinolinyl, isoquinolinyl, tetrahydroisoquinolinyl, quinoxalinyl, quinazolinyl, naphthyridinyl, indazolyl, indolyl, 2-indolonyl, benzisoxazolyl, benzoisothiazolyl, benzoxazolyl, benzothiazolyl, benzimidazolyl, furopyridinyl, thienopyridinyl, thienopyrimidinyl, isothiazolopyridinyl, thiazolopyridinyl, thiazolopyridinonyl, thiazolopyrazinyl, thiazolopyrimidinyl, triazolopyridinyl, triazolopyrazinyl, pyrrolotriazinyl, 5,6-dihydrobenzo[h]quinazolinyl, 5H-chromeno[4,3-d]pyrimidinyl, 6,7-dihydro-5H-cyclopenta[d]pyrimidinyl, 5,6,7,8-tetrahydroquinazolinyl, 7,8-dihydroquinazolin-5(6H)-onyl, and tetrahydrobenzothiazolyl, and is substituted with 0-3 substituents independently selected from the group consisting of $C_{1-4}$alkyl, $C_{3-7}$cycloalkyl, $C_{1-4}$haloalkyl, $C_{1-4}$alkoxy, $C_{1-4}$haloalkoxy, $C_{3-7}$cycloalkoxy, $C_{1-4}$alkylthio, phenoxy, benzyloxy, halo, hydroxy, cyano, nitro, $C_{1-4}$alkylsulfonyl, $NR^2R^3$, pyrrolidinonyl, methylenedioxy, furyl, thienyl, pyrazolyl, imidazolyl, thiazolyl, triazolyl, pyrazinyl, pyrimidinyl, naphthyl, $C_{1-4}$alkylamido, $CONR^2R^3$, pyridyl, phenyl, and benzyl, and where imidazolyl, pyridyl, phenyl and benzyl are substituted with 0-2 substituents independently selected from the group consisting of halo, $C_{1-4}$alkyl, $C_{1-4}$alkoxy, $C_{1-4}$haloalkoxy, $C_{1-4}$haloalkoxy, and $NR^2R^3$;

$R^2$ is hydrogen, $C_{1-4}$alkyl, $C_{1-4}$hydroxyalkyl, or $C_{1-4}$aminoalkyl;

$R^3$ is hydrogen, $C_{1-4}$alkyl, $C_{1-4}$hydroxyalkyl, or $C_{1-4}$aminoalkyl;

or $R_2$ and $R_3$ taken together with the nitrogen atom to which they are attached is axetidinyl, pyrrolidinyl, piperidinyl, piperazinyl, N—($C_{1-4}$alkyl)piperazinyl, morpholinyl, or homopiperidinyl; and n is 1 or 2;

or a pharmaceutically acceptable salt thereof.

Another aspect of the invention is a stereoisomer of formula I according to the following formula.

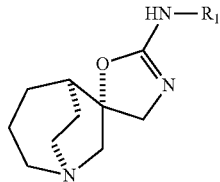

Another aspect of the invention is a stereoisomer of formula I according to the following formula.

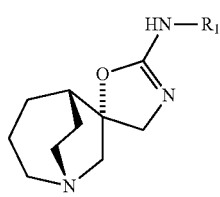

Another aspect of the invention is a stereoisomer of formula I according to the following formula.

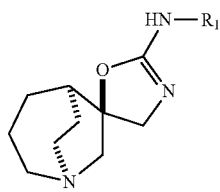

Another aspect of the invention is a stereoisomer of formula I according to the following formula.

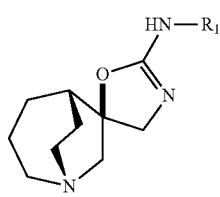

Another aspect of the invention is a stereoisomer of formula I according to the following formula.

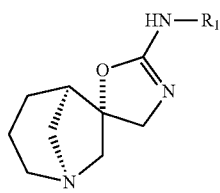

Another aspect of the invention is a stereoisomer of formula I according to the following formula.

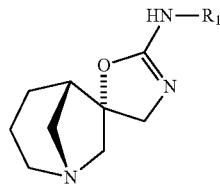

Another aspect of the invention is a stereoisomer of formula I according to the following formula.

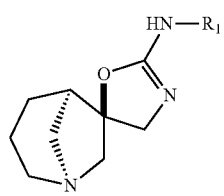

Another aspect of the invention is a stereoisomer of formula I according to the following formula.

Another aspect of the invention is a compound of formula I where $R^1$ is selected from the group consisting of dimethylisoxazolyl, (methyl)(phenyl)isoxazolyl, methylpyrazolyl, dimethylpyrazolyl, thienylpyrazolyl, methoxyphenylpyrazolyl, thiazolyl, bromothiazolyl, cyanothiazolyl, methylthiazolyl, dimethylthiazolyl, (methyl)(phenyl)thiazolyl, isopropylthiazolyl, butylthiazolyl, benzylthiazolyl, methoxyphenylmethylthiazolyl, phenylthiazolyl, chlorophenylthiazolyl, methoxyphenylthiazolyl, (methoxyphenyl)(methyl)thiazolyl, pyridinylthiazolyl, (phenyl)(methyl)imidazolyl, methyloxadiazolyl, ethyloxadiazolyl, methylthiadiazolyl, fluorophenylthiadiazolyl, furylthiadiazolyl, (dimethylcarboxamido)(methyl)thiazolyl, (pyrrolidinylCO)thiazolyl, phenyltriazolyl, pyridinyl, bromopyridinyl, chloropyridinyl, (chloro)(fluoro)pyridinyl, (chloro)(methyl)pyridinyl, dichloropyridinyl, fluoropyridinyl, cyanopyridinyl, (cyano)(methyl)pyridinyl, (cyano)(dimethyl)pyridinyl, methoxypyridinyl, (methylpyrrolidinyl)pyridinyl, phenylpyridinyl, methoxypyridinylpyridinyl, pyridazinyl, bromopyridazinyl, chloropyridazinyl, methylpyridazinyl, methoxypyridazinyl, methylthiopyridazinyl, pyrrolidinylpyridazinyl, pyrrolidinonylpyridazinyl, phenylpyridazinyl, pyridinylpyridazinyl, rnethoxypyridinylpyridazinyl, pyrimidinyl, (bromo)(isopropyl)pyrimidinyl, (bromo)(dimethyl)pyrimidinyl, (bromo)(cyclopropyl)pyrimidinyl, (bromo)(methoxy)pyrimidinyl, (bromo)(phenyl)pyrimidinyl, (bromo)(pyridinyl)pyrimidinyl, chloropyrimidinyl, (chloro)(dimethyl)pyrimidinyl, (methyl)(methoxy)pyrimidinyl, methylpyrimidinyl, ethylpyrimidinyl, (methyl)(phenyl)pyrimidinyl, dimethylpyrimidinyl, butylpyrimidinyl, isopropylpyrimidinyl, cyclopropylpyrimidinyl, methoxypyrimidinyl, dimethoxypyrimidinyl, isopropoxypyrimidinyl, cyclopentoxypyrimidinyl, difluoromethoxypyrimidinyl, trifluoroethoxypyrimidinyl, phenoxypyrimidinyl, methylthiopyrimidinyl, phenylpyrimidinyl, chlorophenylpyrimidinyl, methylphenylpyrimidinyl, methoxyphenylpyrimidinyl, (phenyl)(triazolyl)pyrimidinyl, pyridinylpyrimidinyl, methoxypyridinylpyrimidinyl, methoxypyrimidinylpyrimidinyl, naphthylpyrimidinyl, pyrazinyl, bromopyrazinyl, (bromo)(methoxy)pyrazinyl, chloropyrazinyl, methylpyrazinyl, dimethylpyrazinyl, butylpyrazinyl, cyanopyrazinyl, methoxypyrazinyl, isopropoxypyrazinyl, trifluoromethylpyrazinyl, and phenylpyrazinyl, and dimethyltriazinyl; or a pharmaceutically acceptable salt thereof.

Another aspect of the invention is a compound of formula I where $R^1$ is selected from the group consisting of dimethylpyridinoisoxazolyl, benzoxazolyl, chlorobenzoxazolyl, fluorophenylbenzoxazolyl, ethylphenylbenzoxazolyl, dimethylaminophenylbenzoxazolyl, pyridinylbenzoxazolyl, benzothiazolyl, acetamidobenzothiazolyl, bromobenzothiazolyl, chlorobenzothiazolyl, (chloro)(methyl)benzothiazolyl, (chloro)(methoxy)benzothiazolyl, fluorobenzothiazolyl, difluorobenzothiazolyl, cyanobenzothiazolyl, methylbenzothiazolyl, dimethylbenzothiazolyl, (methyl)(methoxy)benzothiazolyl, ethylbenzothiazolyl, trifluoromethylbenzothiazolyl, hydroxybenzothiazolyl, methoxybenzothiazolyl, ethoxybenzothiazolyl, isopropoxybenzothiazolyl, trifluoromethoxybenzothiazolyl, difluoromethoxybenzothiazolyl, dimethoxybenzothiazolyl, morpholinylbenzothiazolyl, (pyrrolidinylCO)benzothiazolyl, methylsulfonylbenzothiazolyl, chlorothiazolopyridinyl, dimethylthiazolopridinyl, benzyloxythiazolopyridinyl, difluoromethoxythiazolopyridinyl, benzotriazolyl, indolonyl, indazolyl, bromoindazolyl, chloroindazolyl, fluoroindazolyl, (methyl)(methoxy)indazolyl, methoxyindazolyl, trifluoromethylindazolyl, trifluoromethoxyindazolyl, difluoromethoxyindazolyl, benzimidazolyl, fluorobenzimidazolyl, methylbenzimidazolyl, (methyl)(methoxy)benzimidazolyl, methoxybenzimidazolyl, tetrahydrobenzothiazolyl, furopyridinyl, dimethylfuropyrimidinyl, thienopyrimidinyl, isopropylthienopyrimidinyl, dimethylthienopyrimidinyl, ehlortriazolopyridinyl, methyltriazolopyridinyl, trifluoromethyltriazolopyridinyl, methoxytriazolopyridinyl, triazolopyrazinyl, bromopyrrolotriazinyl, dimethylaminothiazolopyrimidinyl, thiazolopyazinyl, bromothiazolopyazinyl, methoxythiazolopyazinyl, methylthiothiazolopyazinyl, methoxythiazolopyrimidinyl, (methyl)(methoxy)thiazolopyrimidinyl, quinolinyl, bromoquinolinyl, fluoroquinolinyl, methylquinolinyl, (methyl)(methoxy)quinolinyl, isoquinolinyl, bromoisoquinolinyl, dichloroisoquinolinyl, methylisoquinolinyl, dimethylisoquinolinyl, quinoxalinyl, chloroquinoxalinyl, methylquinoxalinyl, methoxyquinoxalinyl, quinazolinyl, bromoquinazolinyl, naphthyridinyl, 5,6-dihydrobenzo[h]quinazolinyl, 5H-chromeno[4,3-d]pyrimidinyl, 6,7-dihydro-5H-cyclopenta[d]pyrimidinyl, 5,6,7,8-tetrahydroquinazolinyl, and 7,8-dihydroquinazolin-5(6H)-onyl; or a pharmaceutically acceptable salt thereof.

Another aspect of the invention is a compound of formula I where $R^1$ is selected from the group consisting of phenylthiazolyl, (chloro)(methyl)pyridinyl, (bromo)(phenyl)pyrimidinyl, methoxypyrimidinyl, difluoromethoxypyrimidinyl, difluoroethoxypyrimidinyl, cyclopentoxypyrimidinyl, (methylphenyl)pyrimidinyl, (methoxyphenyl)pyrimidinyl, bromopyrazinyl, chloropyrazinyl, methylthiopyrazinyl, methoxybenzothiazolyl, ethoxybenzothiazolyl, difluoromethoxybenzothiazolyl, thiazolopyridinonyl, trifluoromethylindazolyl, benzimidazolyl, isoquinoinyl, and quinazolinyl or a pharmaceutically acceptable salt thereof.

Another aspect of the invention is a compound or formula I where $R^1$ is selected from the group consisting of thiazolyl, pyridinyl, pyridazinyl, pyrimidinyl, pyrazinyl, benzothiazolyl, thiazolopyridinyl, indazolyl, benzimidazolyl, isoquinolinyl, and quinazolinyl, and is substituted with 0-3 substituents independently selected from the group consisting of $C_{1-4}$alkyl, $C_{3-7}$cycloalkyl, $C_{1-4}$haloalkyl, $C_{1-4}$alkoxy, $C_{1-4}$haloalkoxy, $C_{3-7}$cycloalkoxy, $C_{1-4}$alkylthio, phenoxy, benzyloxy, halo, hydroxy, cyano, $C_{1-4}$alkylsulfonyl, $NR^2R^3$, pyrrolidinonyl, methylenedioxy, furyl, thienyl, triazolyl, pyrimidinyl, naphthyl, $C_{1-4}$alkylamido, $CONR^2R^3$, pyridyl, phenyl, and benzyl, and where pyridyl, phenyl and benzyl are substituted with 0-2 substituents independently selected from the group consisting of halo, $C_{1-4}$alkyl, $C_{1-4}$alkoxy, $C_{1-4}$haloalkyl, $C_{1-4}$haloalkoxy, and $NR^2R^3$; or a pharmaceutically acceptable salt thereof.

Another aspect of the invention is a compound or formula I where $R^1$ is selected from the group consisting of pyridinyl, pyrimidinyl, pyrazinyl, thiazolopyridinyl, and isoquinolinyl, and is substituted with 0-3 substituents independently selected from the group consisting of $C_{1-4}$alkyl, $C_{3-7}$cycloalkyl, $C_{1-4}$haloalkyl, $C_{1-4}$alkoxy, $C_{1-4}$haloalkoxy, $C_{3-7}$cycloalkoxy, $C_{1-4}$alkylthio, phenoxy, benzyloxy, halo, hydroxy, cyano, $C_{1-4}$alkylsulfonyl, $NR^2R^3$, pyrrolidinonyl, methylenedioxy, furyl, thienyl, triazolyl, pyrimidinyl, naphthyl, $C_{1-4}$alkylamido, $CONR^2R^3$, pyridyl, phenyl, and benzyl, and where pyridyl, phenyl and benzyl are substituted with 0-2 substituents independently selected from the group consisting of halo, $C_{1-4}$alkyl, $C_{1-4}$alkoxy, $C_{1-4}$haloalkyl, $C_{1-4}$haloalkoxy, and $NR^2R^3$; or a pharmaceutically acceptable salt thereof.

Another aspect of the invention is a compound or formula I where $R^1$ is selected from the group consisting of pyridinyl and isoquinolinyl, and is substituted with 0-3 substituents independently selected from the group consisting of $C_{1-4}$alkyl, $C_{3-7}$cycloalkyl, $C_{1-4}$haloalkyl, $C_{1-4}$alkoxy, $C_{1-4}$haloalkoxy, $C_{3-7}$cycloalkoxy, $C_{1-4}$alkylthio, phenoxy, benzyloxy, halo, hydroxy, cyano, $C_{1-4}$alkylsulfonyl, $NR^2R^3$, pyrrolidinonyl, methylenedioxy, furyl, thienyl, triazolyl, pyrimidinyl, naphthyl, $C_{1-4}$alkylamido, $CONR^2R^3$, pyridyl, phenyl, and benzyl, and where pyridyl, phenyl and benzyl are substituted with 0-2 substituents independently selected from the group consisting of halo, $C_{1-4}$alkyl, $C_{1-4}$alkoxy, $C_{1-4}$haloalkyl, $C_{1-4}$haloalkoxy, and $NR^2R^3$; or a pharmaceutically acceptable salt thereof.

Another aspect of the invention is a compound of formula I where $R^1$ is selected from the group consisting of pyridinyl, pyrimidinyl, pyrazinyl, thiazolopyridinyl, isoquinolinyl, and benzoxazolyl, and is substituted with 0-3 substituents independently selected from the group consisting of $C_{1-4}$alkyl, $C_{3-7}$cycloalkyl, $C_{1-4}$haloalkyl, $C_{1-4}$alkoxy, $C_{1-4}$haloalkoxy, $C_{3-7}$cycloalkoxy, halo, hydroxy, cyano, $NR^2R^3$, pyrrolidinonyl, methylenedioxy, furyl, thienyl, triazolyl, imidazolyl, thiazolyl, oxazolyl, pyrimidinyl, naphthyl, $C_{1-4}$alkylamido, $CONR^2R^3$, pyridyl, and phenyl, and where pyridyl, phenyl, thiazolyl and imidazolyl are substituted with 0-2 substituents independently selected from the group consisting of halo, $C_{1-4}$alkyl, $C_{1-4}$alkoxy, $C_{1-4}$haloalkoxy, and $NR^2R^3$; or a pharmaceutically acceptable salt thereof.

Another aspect of the invention is a compound selected from the group consisting of (5S*,5'R*)—N-(benzo[d]thiazol-2-yl)-4'H-1-azaspiro[bicyclo[3.2.1]octane-6,5'-oxazol]-2'-amine, (5S*,5'R*)—N-(6-methoxybenzo[d]thiazol-2-yl)-4'H-1-azaspiro[bicyclo[3.2.1]octane-6,5'-oxazol]-2'-amine, (5S*,5'R*)—N-(thiazolo[5,4-b]pyridin-2-yl)-4'H-1-azaspiro[bicyclo[3.2.1]octane-6,5'-oxazol]-2'-amine, (5S*,5'R*)—N-(isoquinolin-3-yl)-4'H-1-azaspiro[bicyclo[3.2.1]octane-6,5'-oxazol]-2'-amine, (5R*,5'R*)—N-(thiazolo[5,4- b]pyridin-2-yl)-4'H-1-azaspiro[bicyclo[3.2.1]octane-6,5'-oxazol]-2'-amine; or a pharmaceutically acceptable salt thereof.

For a compound of formula I, the scope of any instance of a variable substituent, including $R^1$, $R^2$, and $R^3$, can be used independently with the scope of any other instance of a variable substituent. As such, the invention includes combinations of the different aspects.

Unless specified otherwise, these terms have the following meanings. "Alkyl" means a straight or branched alkyl group composed of 1 to 4 carbons. "Alkenyl" means a straight or branched alkyl group composed of 2 to 4 carbons with at least one double bond. "Alkynyl" means a straight or branched alkyl group composed of 2 to 4 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art.

The invention includes all tautomeric fowls of the compounds. An example of a tautomeric pair is shown below.

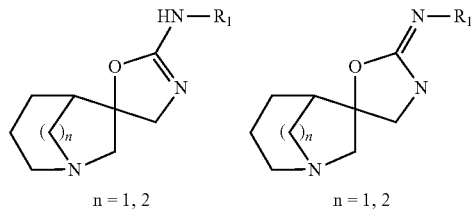

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Some of the compounds may be prepared using the reactions and techniques described in this section. The reactions are performed in solvents appropriate to the reagents and materials employed and are suitable for the transformations being effected. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC" for t-butoxycarbonyl, "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et₂O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for $CF_3(CF_2)_3SO_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "cone." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "¹H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Scheme 1.

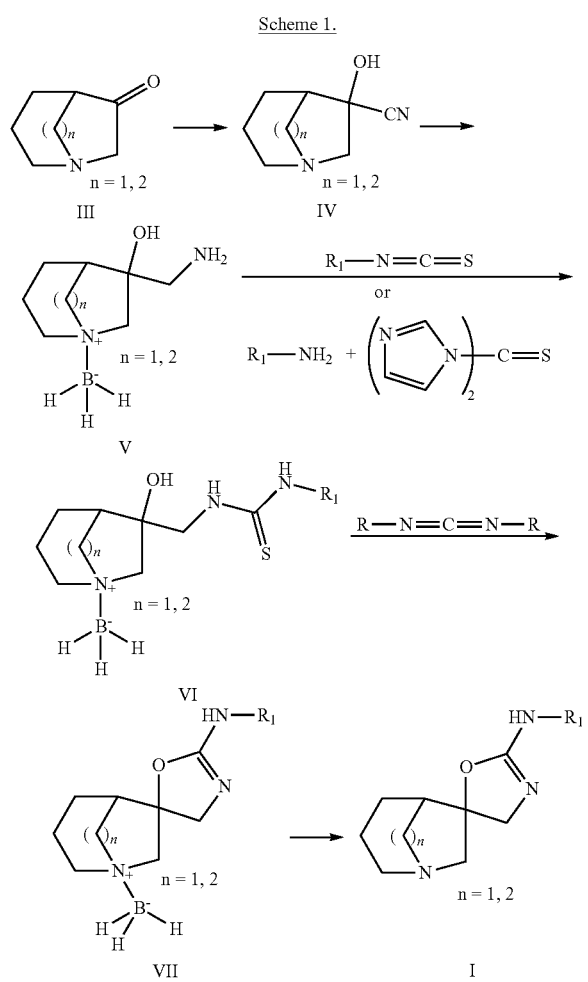

Scheme 2.

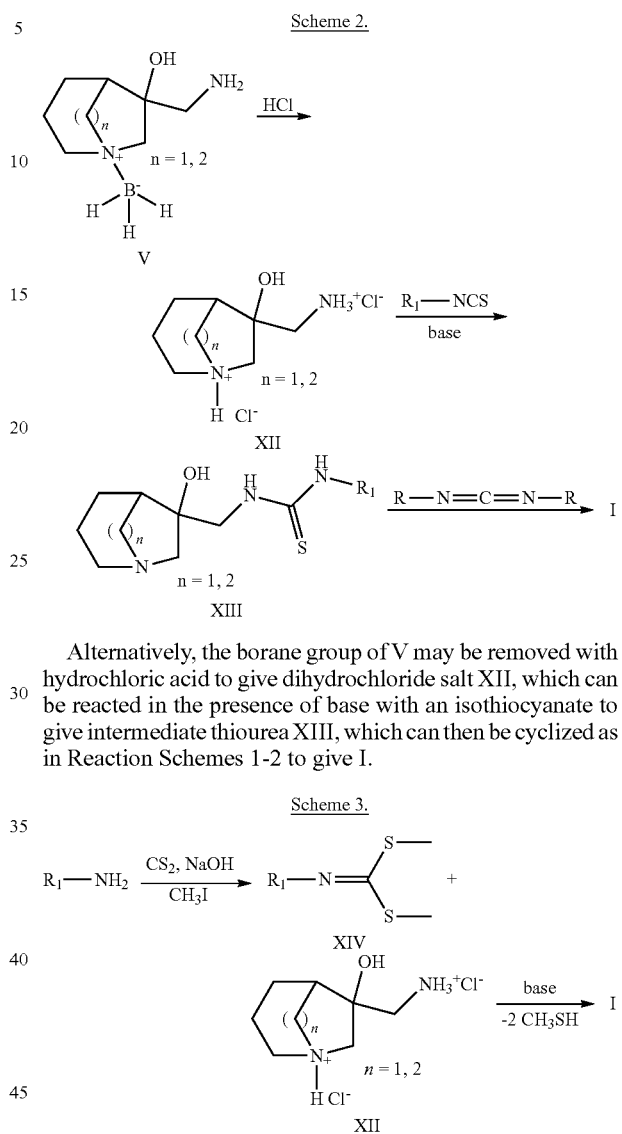

Some compounds of Formula I can be prepared as illustrated in Reaction Scheme I. The ketone of Formula III is known and may be prepared by methods known to those skilled in the art. The ketone can be converted to the corresponding cyanohydrin of Formula IV by reaction with sodium or potassium cyanide plus an acid. The compound of Formula IV can be reduced to the corresponding aminomethyl compound (borane complex) of Formula V by reaction with borane/tetrahydrofuran complex.

The compound of Formula V can be reacted with heteroaryl isothiocyanates directly in an inert solvent to give the thioureas of Formula VI. Alternatively, the heteroarylamine can be reacted with thiocarbonyl-diimidazole to give an activated species which can be used without isolation to convert the compound of Formula V to the compound of Formula VI. The heteroarylamine may be prepared by methods known to those skilled in the art.

The thiourea of Formula VI can be cyclized using, for example, di-isopropyl carbodiimide to give the oxazoline of Formula VII which may be deprotected via treatment with acid to give the racemic final product of the compound of Formula I. The compound of Formula I may be resolved into pure enantiomer compounds by means known in the art, for example, via chiral chromatography.

The borane group in the compound of Formula X can be removed, for example, by treatment with dilute hydrochloric acid to give the chiral quinuclidine amine of Formula XI. Similarly to Reaction Scheme 1, the amine salt of Formula XI can be reacted with isothiocyanates to give the thiourea of Formula VIa, which can then be reacted with dialkyl carbodiimides or mixed thioureas (as from reaction with thiocarbonyl diimidazole) to give the chiral oxazoline quinuclidine compounds of Formula I.

Alternatively, the borane group of V may be removed with hydrochloric acid to give dihydrochloride salt XII, which can be reacted in the presence of base with an isothiocyanate to give intermediate thiourea XIII, which can then be cyclized as in Reaction Schemes 1-2 to give I.

Scheme 3.

Additionally, the (hetero)aromatic amines may be reacted with carbon disulfide, sodium hydroxide, and methyl iodide to give intermediate dimethyl carbonimidodithioates XIV. These are reacted with dihydrochloride XI in the presence of base to eliminate two moles of methanethiol and generate desired products I directly.

Biological Methods

I) α7 Nicotinic Acetycholine Receptor Binding.

Membranes were prepared for binding using HEK293 cells stably expressing the rat α7 nicotinic acetylcholine receptor (rat α7 nAChR). Cells were homogenized at 4° C. in hypotonic lysis buffer consisting of 10 mM Tris (pH 7.4), 5 mM EDTA and protease inhibitors and centrifuged at 32000×g for 20 minutes. The pellet was washed once in membrane wash buffer consisting of 50 mM Tris (pH 7.4), 1 mM EDTA and protease inhibitors and centrifuged at 32000×g for 20 minutes. This pellet was then resuspended in assay buffer consisting 50 mM $KH_2PO_4$ (pH 7.4 at 25° C.), 1 mM EDTA, 0.005% Triton-X 100 and 0.1% (v/v) Sigma Protease Inhibitor Cocktail. Aliquots were then frozen in dry ice/ethanol and kept at −80° C. until the day of the assay.

II) A $Ca^{2+}$-Sensitive, Fluorescence-Based Assay α-7 for Nicotinic Acetylcholine Receptor Channel Function In Mammalian Cells ("FLIPR").

Summary:

Lead compounds are evaluated for agonist activity at α-7, α3β4, α4αβ2, and α1β1δ1ε sub-types of nicotinic ACh receptor ion channels expressed in mammalian HEK 293 cells. Agonist potency and efficacy values are determined from kinetic fluorescence $Ca^{2+}$ influx measurements made using a 384 well FLIPR (Fluorescence Image Plate Reader). The utility of fluorescent indicators for measuring changes in intracellular divalent cation concentrations, particularly $Ca^{2+}$, for drug discovery endeavors is well documented (Rudiger, R., et al., *Nature Reviews*, 2003, 4:579-586; Gonzalez J. E., et al., *Receptors and Channels*, 2002, 8:283-295). In this assay, channel expressing HEK cell lines seeded in 384 well assay plates are loaded with a membrane permeant fluorescent $Ca^{2+}$ indicator dye, whose 510 nm green emission signal increases in response to elevation of intracellular $Ca^{2+}$ concentration. The basal fluorescence from the cells is monitored in real time, followed by the acute addition of test compounds. If the compound is an agonist at any of the non-selective cation channels, the latter open and allow the movement of extracellular $Ca^{2+}$ ions into the cell cytoplasm, where they bind to the $Ca^{2+}$ indicator dye, and produce an increase in fluorescence output signal, which is detected by a cooled CCD imaging camera.

Materials and Methods:

Reagents: The acetomethoxy (AM) ester of the $Ca^{2+}$ indicator dye Fluo-4 was obtained from InVitrogen, (Carlsbad, Calif.). Acetylcholine and all buffer constituents were purchased from Sigma Chemical Company, St. Louis, Mo. G418 and Minimal Essential Medium were purchased from InVitrogen Life Technologies, Carlsbad, Calif. Fetal bovine serum was purchased from (InVitrogen, Carlsbad, Calif.).

Cell Culture:

HEK-293 cells were grown in Minimal Essential Medium containing 10% (v/v) fetal bovine serum at 37° C. in a 5% $CO_2$ incubator. HEK-293 cells stably expressing the ion channels were grown in the same medium with the addition of 500 μg/ml G418.

$Ca^{2+}$ Flux Assays of $Ca^{2+}$ Channels Expressed in HEK-293 Cells:

HEK-293 cells expressing the ion channels of interest were plated in 384 well, black-walled, clear-bottomed, poly-D-lysine coated plates at a density of ~20,000 cells/well in 20 μl of Minimal Essential Medium containing 10% (v/v) fetal bovine serum and incubated for 2 days at 29° C. in a 5% $CO_2$ incubator. Prior to assay, cells were loaded with the Fluo-4 AM ester. Cell loading was accomplished by removing the culture medium and replacing it with 30 μl/well of the AM ester of the dye (5 μM) mixed with Hanks Balanced Salt Solution (#14175-095) containing 20 mM HEPES, 2.5 mM probenecid, 0.5 mM $CaCl_2$, 1 mM MgCl2 and 10 μM atropine. Dye loading was allowed to proceed for 90 minutes at room temperature at which time the dye loading solution was removed and replaced with 40 μl/well of Hanks buffer. Cells loaded with dye were loaded onto a FLIPR384 (Molecular Devices, Sunnyvale, Calif.). Fluo-4 dye was excited using the 488 nm line of an argon laser. Emission was filtered using a 540+/−30 nm bandpass filter. For evaluation of the effects of test compounds using the $Ca^{2+}$ flux assay, compounds to be tested were provided in assay ready plates. For nicotinic receptor ion channel expressing cells, the assay was initiated by the addition of 20 μl/well of Hanks buffer containing test compounds. For all assays, data were collected at 1 Hz for 10 seconds (baseline), at which time the compound containing stimulus buffers are added, and further measurements collected at 0.33 Hz for 3 min.

Data Analysis:

The statistical robustness of the nicotinic receptor $Ca^{2+}$ flux assays is determined from blanks and totals wells. The totals wells define maximal channel activation for each compound test plate (Maximum efficacious dose of acetylcholine), and the blanks wells which contain matched DMSO only, define zero channel activation. The raw fluorescence units data files generated on the FLIPR plate reader are automatically exported and processed by in-house data analysis tools. The reduced percent activation data for each concentration of test compound are fit using MathIQ fitting engine (ID Business Solutions Limited, Surrey, UK). Data were analyzed by fitting maximum amplitudes of change in fluorescence, for $Ca^{2+}$ flux for a given condition of test compound. Potencies ($EC_{50}$ values) of compounds are calculated from the average of three assay wells from a twenty point CRC. Test compound efficacy values (Ymax values) are expressed relative to a maximal response to acetylcholine in the total wells.

III) Fos Quantification Assay:

Male Wistar rats are treated with drug (1-10 mg/kg) or vehicle (2 ml/kg, sc). Two hours after treatments, the rats are rapidly decapitated and discrete brain regions of interest are isolated on ice and weighed and flash frozen with liquid nitrogen and stored at −80 deg. C. Further processing of the brain tissue for nuclear extracts as well as for Fos quantification are in accordance with the protocol prescribed by a commercially available ELISA-based chemiluminiscence detection kit (catalog #89860, EZ-detect c-Fos Trans kit, Pierce Biotechnology Inc., Rockford, Ill.).

IV) MK-801 Disrupted Set-Shift Assay in Rats:

This assay uses a modification of the protocol described by Stefani et al. (*Behavioral Neuroscience*, 2003, 117: 728-737). Test compounds are assessed for their ability to reverse an MK-801-induced performance deficit (0.03 mg/kg, i.p., single dose) in this assay.

The activity of specific compounds described herein and tested in the above assay (II) is provided in Table 1.

TABLE 1

Pharmaceutical Compositions and Methods of Treatment

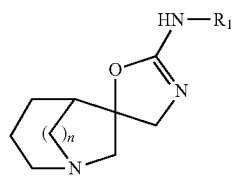

I n = 1, 2

| Example Number | n | $R_1$ | FLIPR α7-HI ($EC_{50}$, nM) | FLIPR α7 actvity rating[a] ($EC_{50}$, nM) |
|---|---|---|---|---|
| 1 | 1 | 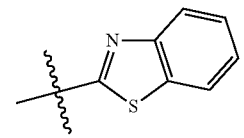 [SMILES: *c1nc2ccccc2s1] | >100000 | + |

TABLE 1-continued

Pharmaceutical Compositions and Methods of Treatment

Formula I: spiro compound with HN—R₁, oxazoline ring, and azacycle (CH₂)ₙ where n = 1, 2

| Example Number | n | R₁ | FLIPR α7-HI (EC$_{50}$, nM) | FLIPR α7 activity rating[a] (EC$_{50}$, nM) |
|---|---|---|---|---|
| 2 | 1 | 6-methoxy-benzothiazol-2-yl | 2050 | ++ |
| 3 | 1 | thiazolo[5,4-b]pyridin-2-yl | 1080 | ++ |
| 4 | 1 | isoquinolin-3-yl | 820 | +++ |
| 5 | 1 | thiazolo[5,4-b]pyridin-2-yl (isomer) | 132 | +++ |
| 5a | 1 | thiazolo[4,5-b]pyridin-2-yl | 105 | +++ |
| 5b | I | thiazolo[4,5-b]pyridin-2-yl | 88 | +++ |

[a] Activity based on EC$_{50}$ nM values: +++ = <100 nM; ++ = 100-1000 nM; + = 1000-100000 nM;
[b] NT = Not tested; NA = Not active (>1000000 nM).

Compounds of formula I bind to alpha 7 and can be useful in treating affective disorders and neurodegenerative disorders. Therefore, another aspect of the invention is a composition comprising a compound of formula I or a pharmaceutically acceptable salt thereof, and a pharmaceutically acceptable carrier.

Another aspect of the invention is the use of a compound of formula I in the manufacture of a medicament for the treatment of affective disorders or neurodegenerative disorders.

Another aspect of the invention is the use of a compound of formula I, in the manufacture of a medicament for the treatment of schizophrenia or Alzheimer's Disease.

Another aspect of the invention is a method of treating affective disorders or neurodegenerative disorders comprising administering to a patient a therapeutically effective amount of a compound of formula I.

Another aspect of the invention is a method of treating schizophrenia or Alzheimer's Disease comprising administering to a patient a therapeutically effective amount of a compound of formula I.

Another aspect of the invention is a method of treating schizophrenia comprising administering to a patient a therapeutically effective amount of a compound of formula I.

Another aspect of the invention is a method of treating Alzheimer's Disease comprising administering to a patient a therapeutically effective amount of a compound of formula I.

Another aspect of the invention is a method of treating cognitive disorders comprising administering to a patient a therapeutically effective amount of a compound of formula I.

Another aspect of the invention is a method of treating rheumatoid arthritis comprising administering to a patient a therapeutically effective amount of a compound of formula I.

Another aspect of the invention is a method of treating osteoarthritis comprising administering to a patient a therapeutically effective amount of a compound of formula I.

Another aspect of the invention is a method of treating ulcerative colitis comprising administering to a patient a therapeutically effective amount of a compound of formula I.

Another aspect of the invention is a method of treating Crohn's Disease comprising administering to a patient a therapeutically effective amount of a compound of formula I.

Another aspect of the invention is a method of treating diabetes comprising administering to a patient a therapeutically effective amount of a compound of formula I.

"Patient" means a person suitable for therapy as understood by practitioners in the field of affective disorders and neurodegenerative disorders.

"Treatment," "therapy," and related terms are used as understood by practitioners in the field of affective disorders and neurodegenerative disorders.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

DESCRIPTION OF SPECIFIC EMBODIMENTS $^1$H-NMR spectra were run on a Broker 500, 400, or 300 MHz instrument and chemical shifts were reported in ppm (δ) with reference to tetramethylsilane (δ=0.0). All evaporations mere carried out under reduced pressure. Unless otherwise stated, LC/MS analyses were carried out on a Shimadzu instrument using a Phenomenex-Luna 4.6×50 mm S 10 reverse phase column employing a flow rate of 4 mL/min using a 0.1% TFA in methanol/water gradient [0-100% in 3 min, with 4 min run time] and a UV detector set at 220 nm or Gemini C18 4.6×50 mm 5 u reverse phase column employing a flow rate of 5 mL/min using a 10 mM ammonium acetate acetonitrile/water gradient [5-95% in 3 min, with 4 min run time] and a UV detector set at 220 nm (negative-ion mass spectrometry). Unless otherwise stated, purification could be done by preparative C-18 column employing gradients of methanol-water containing 0.1% of trifluoroacetic acid (TFA), and using a Shimadzu High Performance Liquid Preparative Chromatographic System employing an XTERRA 30×100 mm S5 column at 40 mL/min flow rate with a 12 min gradient.

EXAMPLE 1

(5S*,5'R*)—N-(benzo[d]thiazol-2-yl)-4'H-1-azaspiro[bicyclo[3.2.1]octane-6,5'-oxazol]-2'-amine

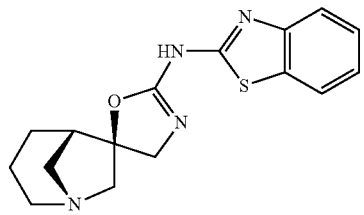 [SMILES: c1ccc2sc(NC3=NC[C@@]4(C[N@]5CCC[C@H]4C5)O3)nc2c1]

Step A: (5S*,6R*)-6-hydroxy-1-azabicyclo[3.2.1]octane-6-carbonitrile

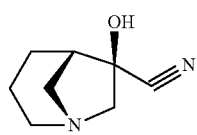 [SMILES: N#C[C@]1(O)C[N@]2CCC[C@H]1C2]

To a vial containing 1-azabicyclo[3.2.1]octan-6-one, HCl (1.0 g, 7.99 mmol) in water (3 mL) was added sodium cyanide (392 mg, 7.99 mmol) dissolved in water (1 mL). The mixture was heated to 50° C. overnight and the resulting precipitate was collected via vacuum filtration to yield (5S*,6R*)-6-hydroxy-1-azabicyclo[3.2.1]octane-6-carbonitrile (790 mg, 65%) as a white solid. $^1$H NMR (400 MHz, DMSO-d$_6$) δ ppm 6.49 (br. s., 1H) 3.25-3.66 (m, 1H) 2.91 (d, J=13.55 Hz, 1H) 2.61-2.87 (m, 4H) 2.15 (br. s., 1H) 1.52-1.88 (m, 3H) 1.34 (d, J=13.55 Hz, 1H).

Step B: ((1R*,5S*,6S*)-6-(aminomethyl)-6-hydroxy-1-ammoniobicyclo[3.2.1]octan-1-yl)trihydroborate

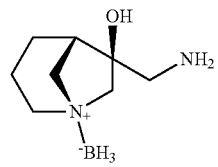

6-Hydroxy-1-azabicyclo[3.2.1]octane-6-carbonitrile (790 mg, 5.19 mmol) was dissolved in THF (5 mL). To this solution was slowly added borane tetrahydrofuran complex (5.19 ml, 5.19 mmol, 1M in THF). After the bubbling ceased, the reaction was stirred at room temperature for 30 minutes and then was treated with borane tetrahydrofuan complex (15.57 ml, 15.57 mmol) again. The reaction was heated to reflux for 4 hours and then cooled to room temperature. The reaction was quenched with the slow addition of ethanol (100 ml) and then allowed to stir at room temperature overnight. The solvent was removed to ((1R*,5S*,6S*)-6-(aminomethyl)-6-hydroxy-1-ammoniobicyclo[3.2.1]octan-1-yl)trihydroborate (376 mg, 42%), which was used as is for the next reaction. $^1$H NMR (400 MHz, DMSO-d$_6$) δ ppm 3.20-3.55 (m, 2H) 3.14 (dd, J=13.30, 1.51 Hz, 1H) 2.79-2.99 (m, 3H) 2.64-2.79 (m, 3H) 1.96-2.05 (m, 1H) 1.02-1.92 (m, 9H).

Step C: N-(Benzo[d]H-imidazole-2-yl)-$^1$H-imidazole-1-carbothioamide

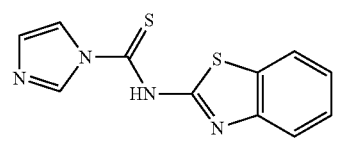 [SMILES: S=C(Nc1nc2ccccc2s1)n1ccnc1]

To benzo[d]thiazol-2-amine (20 g, 133 mmol) in acetonitrile (300 mL) was added 1,1'-thiocarbonyldiimidazole (30.8 g, 173 mmol). The reaction was stirred at 50° C. for 24 hours. The reaction was cooled to room temperature and the precipitate was filtered and washed with acetonitrile (2×50 mL). The yellow powder was dried in a vacuum oven (40° C.) for 2 hours. The product, N-(benzo[d]thiazol-2-yl)-$^1$H-imidazole-1-carbothioamide (28.9 g, 111 mmol), was taken directly to the next step without any further purification.

Step D: (5S*,5'R*)—N-(benzo[d]thiazol-2-yl)-4'H-1-azaspiro[bicyclo[3.2.1]octane-6,5'-oxazol]-2'-amine

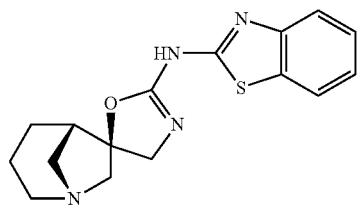 [SMILES: c1ccc2sc(NC3=NC[C@@]4(C[N@]5CCC[C@H]4C5)O3)nc2c1]

((1R*,5S*,6S*)-6-(Aminomethyl)-6-hydroxy-1-ammoniobicyclo[3.2.1]octan-1-yl)trihydroborate (300 mg, 1.76 mmol) and N-(benzo[d]thiazol-2-yl)-1H-imidazole-1-carbothioamide (550 mg, 2.12 mmol) were combined in DMF (5 mL). The reaction was heated to 70° C. for 2 hours and then treated with N,N'-diisopropylcarbodiimide (1.37 mL, 8.82 mmol). The reaction was then heated an additional 2 hours and cooled to room temperature. The reaction was poured into a chloroform/water mixture and the organic was collected and dried to a residue. The residue was taken up in acetone (6 mL) and treated with hydrochloric acid (3 mL, 3M, 9.00 mmol). The reaction was stirred at room temperature for 3 hours and then poured into a chloroform/water mixture. The organic was discarded and the water layer was neutralized to pH 7. The neutralized layer was extracted with chloroform and the chloroform was removed in vacuo to give a crude mixture. This mixture was purified by PREP HPLC. The desired compound fractions were combined and diluted with saturated sodium bicarbonate. The solution was then extracted several times with chloroform. The chloroform layers were combined and concentrated to give (5S*,5'R*)—N-(benzo[d]thiazol-2-yl)-4'H-1-azaspiro[bicyclo[3.2.1]octane-6,5'-oxazol]-2'-amine as a white powder (45.1 mg, 13%) 1H NMR (400 MHz, CHLOROFORM-d) δ ppm 9.17-9.65 (m, 1H) 7.62 (dd, J=13.18, 7.65 Hz, 2H) 7.25-7.37 (m, 1H) 7.11-7.20 (m, 1H) 4.12 (d, J=9.79 Hz, 1H) 3.96-4.06 (m, 1H) 3.59 (d, J=14.31 Hz, 1H) 3.24 (d, J=11.54 Hz, 1H) 3.12 (dd, J=14.31, 2.51 Hz, 1H) 2.79-3.00 (m, 3H) 2.30 (q, J=3.35 Hz, 1H) 1.71-1.92 (m, 2H) 1.33-1.57 (m, 2H) LC/MS RT=0.687 rains [M+H]=315.06.

EXAMPLE 2

(5S*,5'R*)—N-(6-methoxybenzo[d]thiazol-2-yl)-4'H-1-azaspiro[bicyclo[3.2.1]octane-6,5'-oxazol]-2'-amine

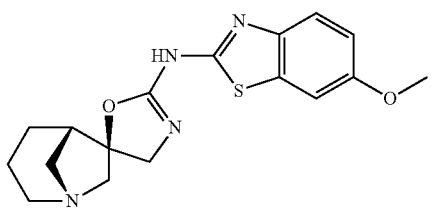 [SMILES: COc1ccc2nc(NC3=NC[C@@]4(C[N@]5CCC[C@H]4C5)O3)sc2c1]

Step A: N-(6-Methoxybenzo[d]thiazol-2-yl)-1H-imidazole-1-carbothioamide

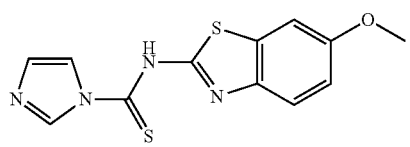 [SMILES: COc1ccc2nc(NC(=S)n3ccnc3)sc2c1]

To 6-methoxybenzo[d]thiazol-2-amine (0.53 g, 2.94 mmol) in acetonitrile (20 mL) was added 1,1'-thiocarbonyldiimidazole (0.681 g, 3.82 mmol). The reaction mixture was stirred at 65° C. for 24 hours. The precipitate was filtered and washed with acetonitrile (2×20 mL) to yield the product. The product was taken directly to the next step without any further purification or characterization.

Step B: (5S*,5'R*)—N-(6-methoxybenzo[d]thiazol-2-yl)-4'H-1-azaspiro[bicyclo[3.2.1]octane-6,5'-oxazol]-2'-amine

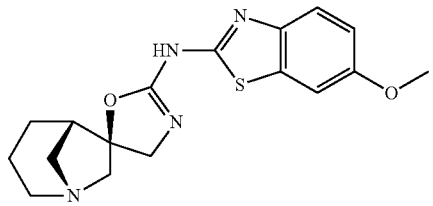 [SMILES: COc1ccc2nc(NC3=NC[C@@]4(C[N@]5CCC[C@H]4C5)O3)sc2c1]

((1R*,5S*,6S*)-(6-(aminomethyl)-6-hydroxy-1-ammoniobicyclo[3.2.1]octan-1-yl)trihydroborate (300 mg, 1.76 mmol) and N-(6-methoxybenzo[d]thiazol-2-yl)-1H-imidazole-1-carbothioamide (615 mg, 2.117 mmol) were combined in DMF (5 mL). The reaction was heated to 70° C. for 2 hours and then treated with N,N'-Diisopropylcarbodiimide (1.37 mL, 8.82 mmol). The reaction was then heated an additional 2 hours and cooled to room temperature. The reaction was poured into a chloroform/water mixture and the organic was collected and dried to a residue. The residue was taken up in acetone (6 ml) and treated with hydrochloric acid (3 mL, 3M, 9.00 mmol). The reaction was stirred at room temperature for 3 hours and then poured into a chloroform/water mixture. The organic was discarded and the water layer was neutralized to pH 7. The neutralized layer was extracted in chloroform and the chloroform was removed in vacco to give a crude mixture. This mixture was purified by PREP HPLC. The desired compound fractions were combined and diluted with saturated sodium bicarbonate. The solution was then extracted several times with chloroform. The chloroform layers were combined and concentrated to give N-(6-methoxybenzo[d]thiazol-2-yl)-4'H-1-azaspiro[bicyclo[3.2.1]octane-6,5'-oxazol]-2'-amine as a white powder (13.1.1 mg, 3%). 1H NMR (400 MHz, CHLOROFORM-d) δ ppm 9.04-9.55 (m, 1H) 7.50 (d, J=8.78 Hz, 1H) 7.15 (d, J=2.51 Hz, 1H) 6.91 (dd, J=8.91, 2.64 Hz, 1H) 4.11 (d, J=9.79 Hz, 1H) 3.97-4.07 (m, 1H) 3.76-3.88 (m, 3H) 3.64 (d, J=14.31 Hz, 1H) 3.29 (br. s., 1H) 3.16 (d, J=14.31 Hz, 1H) 2.87-3.06 (m, 3H) 2.35 (d, J=2.76 Hz, 1H) 1.70-1.96 (m, 2H) 1.38-1.63 (m, 2H). MS: LC/MS RT=0.923 mins [M+H]=345.08.

EXAMPLE 3

(5S*,5'R*)—N-(thiazolo[5,4-b]pyridin-2-yl)-4'H-1-azaspiro[bicyclo[3.2.1]octane-6,5'-oxazol]-2'-amine

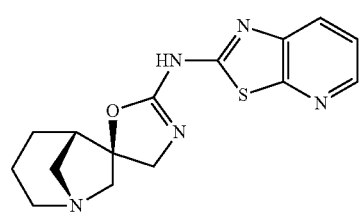 [SMILES: c1cnc2sc(NC3=NC[C@@]4(C[N@]5CCC[C@H]4C5)O3)nc2c1]

Step A: (5S*,6S*)-6-(aminomethyl)-1-azabicyclo[3.2.1]octan-6-ol dihydrochloride

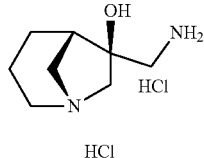 [SMILES: NC[C@]1(O)C[N@]2CCC[C@H]1C2 ; Cl ; Cl]

((1R*,5S*,6S*)-(6-(aminomethyl)-6-hydroxy-1-ammoniobicyclo[3.2.1]octan-1-yl)trihydroborate (400 mg, 2.352 mmol) was dissolved in MeOH (25 mL) and 3N aq. HCl (8 mL, 24.00 mmol) was added, and the mixture was warmed to 50° C. for 2 hours. At that time, the reaction was cooled to room temperature, evaporated to dryness and triturated with EtOH to afford 6-(aminomethyl)-1-azabicyclo[3.2.1]octan-6-ol, 2 HCl (240 mg, 44.5% yield) as a white solid. 1H NMR (400 MHz, DMSO-$d_6$) δ ppm 11.13 (br. s., 1H) 8.23 (br. s., 3H) 6.10 (s, 1H) 3.65 (d, J=13.30 Hz, 2H) 3.23-3.46 (m, 3H) 2.93-3.25 (m, 3H) 2.39 (d, J=2.76 Hz, 1H) 1.80-2.04 (m, 1H) 1.52-1.82 (m, 3H).

Step B: Dimethyl thiazolo[5,4-b]pyridin-2-ylcarbonimidodithioate

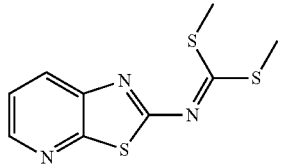

To a suspension of thiazolo[5,4-b]pyridin-2-amine (300 mg, 1.98 mmol) in DMF (2 mL) was added 20.0M sodium hydroxide (200 μL, 4.0 mmol). The mixture was allowed to stir 10 min at room temperature at which time carbon disulfide was added (300 μL, 4.96 mmol) and the resulting reddish brown mixture was stirred for 10 minutes. An additional portion of 20 M sodium hydroxide (200 μL, 4.0 mmol) was added and the mixture was again stirred for 10 minutes. Finally, iodomethane (300 μL, 4.76 mmol) was added dropwise. The mixture was stirred for 5 minutes, at which time a voluminous yellow precipitate had formed. The mixture was poured into water and the solids were collected by filtration to afford dimethyl thiazolo[5,4-b]pyridin-2-ylcarbonimidodithioate (190 mg, 38% yield) as a yellow solid of sufficient purity to use without further purification. $^1$H NMR (500 MHz, CDCl$_3$) δ ppm 8.47 (d, J=4.58 Hz, 1H) 8.11 (dd, J=8.24, 1.53 Hz, 1H) 7.37 (dd, J=8.24, 4.88 Hz, 1H) 2.66 (s, 6H).

Step C: (5S*,5'R*)—N-(thiazolo[5,4-b]pyridin-2-yl)-4'H-1-azaspiro[bicyclo[3.2.1]octane-6,5'-oxazol]-2'-amine

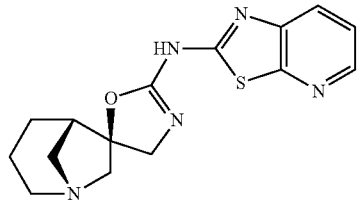 [SMILES: c1cnc2sc(NC3=NC[C@@]4(C[N@]5CCC[C@H]4C5)O3)nc2c1]

To (5S*,6S*)-6-(aminomethyl)-1-azabicyclo[3.2.1]octan-6-ol dihydrochloride (100 mg, 0.436 mmol) in DMF (4 mL) was added dimethyl thiazolo[5,4-b]pyridin-2-ylcarbonimidodithioate (111 mg, 0.44 mmol) and cesium carbonate (427 mg, 1.31 mmol). The reaction was heated to 80° C. for 3 hours and then cooled to room temperature. The reaction was poured into water and chloroform and the organic layer was collected. This was further purified by silica gel chromatography, eluting in 5-40% (10% NH$_4$OH/methanol) in chloroform. The product (5S*,5R*)—N-(thiazolo[5,4-b]pridin-2-yl)-4'H-1-azaspiro[bicyclo[3.2.1]octane-6,5'-oxazol]-2'-amine (34 mg, 0.108 mmol, 24%) was isolated off the column and concentrated to a tan solid. $^1$H NMR (400 MHz, DMSO-$d_6$) δ ppm 9.27 (br. s., 1H) 8.31 (dd, J=4.77, 1.51 Hz, 1H) 7.91 (dd, J=8.28, 1.51 Hz, 1H) 7.39 (dd, J=8.03, 4.77 Hz, 1H) 4.00-4.13 (m, 2H) 3.14-3.32 (m, 2H) 2.92 (s, 2H) 2.64-2.86 (m, 2H) 2.18 (d, J=2.01 Hz, 1H) 1.69-1.85 (m, 2H) 1.24-1.57 (m, 2H). MS: (LC/MS) RT=1.053 mins [M+H]=314.11.

EXAMPLE 4

(5S*,5'R*)—N-(isoquinolin-3-yl)-4'H-1-azaspiro[bicyclo[3.2.1]octane-6,5'-oxazol]-2'-amine

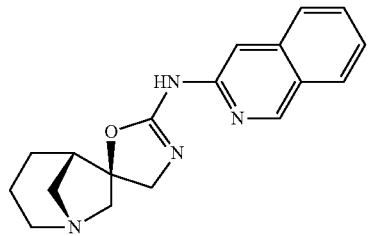 [SMILES: c1ccc2cc(NC3=NC[C@@]4(C[N@]5CCC[C@H]4C5)O3)ncc2c1]

Step A: 3-Isothiocyanatoisoquinoline

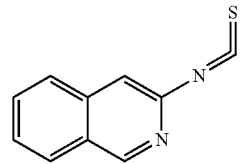 [SMILES: S=C=Nc1cc2ccccc2cn1]

To a solution of 1,1'-thiocarbonyldipyridin-2(1H)-one (0.805 g, 3.47 mmol) in dichloromethane at room temperature was added isoquinolin-3-amine (0.5 g, 3.47 mmol). The reaction was stirred at room temperature for 18 hours. The LC/MS showed the desired product peak a major peak. The deep orange solution was concentrated and filtered. The filtrate was purified by silica gel chromatography (0-40% ethyl acetate-hexanes) to afford 4-isothioeyanato-6-(3-methoxyphenyl)pyrimidine (0.55 g, 2.96 mmol, 85% yield) a white solid. LCMS R.T.=2.47; [M+H]$^+$=187.23.

Step B: (5S*,5'R*)—N-(isoquinolin-3-yl)-4'H-1-azaspiro[bicyclo[3.2.1]octane-6,5'-oxazol]-2'-amine

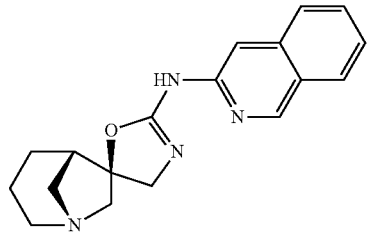 [SMILES: c1ccc2cc(NC3=NC[C@@]4(C[N@]5CCC[C@H]4C5)O3)ncc2c1]

To (5S*,6S*)-6-(aminomethyl)-1-azabicyclo[3.2.1]octan-6-ol dihydrochloride (84 mg, 0.54 mmol) in DMF (3 mL) was added 3-isothiocyanatoisoquinoline (100 mg, 0.54 mmol) and cesium carbonate (526 mg, 1.61 mmol). The reaction was heated to 80° C. for 2 hours and then treated with 1,3-diisopropylcarbodiimide (0.168 mL, 1.08 mmol). The reaction was maintained at 80° C. for 18 hours and then cooled to room temperature. The crude reaction was purified by silica gel chromatography, eluting with 5-40% (10% NH₄OH/methanol) in chloroform. The desired product was collected and concentrated to give (5S*,5'R*)—N-(isoquinolin-3-yl)-4'H-1-azaspiro[bicyclo[3.2.1]octane-6,5'-oxazol]-2'-amine as a yellow solid (34 mg, 20% yield). ¹H NMR (400 MHz, CHLOROFORM-d) δ ppm 9.15 (br. s., 1H) 8.96 (s, 1H) 7.86 (d, J=8.03 Hz, 1H) 7.70 (d, J=8.28 Hz, 1H) 7.55 (t, J=7.28 Hz, 1H) 7.31-7.42 (m, 2H) 4.10 (d, J=9.03 Hz, 1H) 3.96 (d, J=9.03 Hz, 1H) 3.60 (d, J=14.05 Hz, 1H) 3.31 (d, J=11.80 Hz, 1H) 3.09 (dd, J=14.05, 2.01 Hz, 1H) 2.81-3.01 (m, 3H) 2.30 (d, J=3.01 Hz, 1H) 1.74-1.91 (m, 2H) 1.42-1.58 (m, 2H). MS: (LC/MS) RT=0.797 mins [M+H]=309.01.

EXAMPLE 5

(5R*,5'R*)—N-(thiazolo[5,4-b]pyridin-2-yl)-4'H-1-azaspiro[bicyclo[3.2.1]octane-6,5'-oxazol]-2'-amine

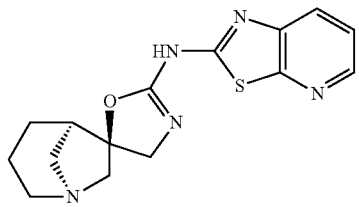 [SMILES: c1cnc2sc(NC3=NC[C@@]4(C[N@@]5CCC[C@@H]4C5)O3)nc2c1]

In a vial was added 1-azabicyclo[3.2.1]octan-6-one, HCl (1.0 g, 7.99 mmol) in water (3 mL). The reaction was cooled to 0° C. and then sodium cyanide (392 mg, 7.99 mmol) dissolved in water (1 mL) was added to the reaction slowly. The reaction was allowed to stir at 0° C. for 10 minutes and then the resulting precipitate was collected via vacuum filtration. The resulting white powder (1.1 g) was immediately dissolved in THF (2 mL) and treated with borane tetrahydrofuran complex (7.23 mL, 7.23 mmol, 1M). After the addition was complete, the reaction is allowed to stir at room temperature for 10 minutes and then treated with additional borane tetrahydrofuran complex (21.68 mL, 21.68 mmol). The reaction is then heated to reflux for 3 hours and cooled to room temperature. The reaction is quenched with ethanol (100 mL) and allowed to stir overnight at room temperature. The solvent is removed in memo and the resulting residue is dissolved in methanol (6 mL) and treated with 3N HCl (3 mL). The mixture is heated to 50° C. for 1 hour and then concentrated to a white crunchy solid (1.0 g).

The foregoing white solid (200 mg) was then dissolved in DMF (4 ml) and treated with dimethyl thiazolo[5,4-b]pyridin-2-ylcarbonimidodithioate (223 mg, 0.873 mmol) and cesium carbonate (853 mg, 2.62 mmol). The reaction was heated to 80° C. for 3 hours and then cooled to room temperature. The reaction was diluted with water (10 mL) and the resulting precipitate was collected by filtration. The solids were then dissolved n chloroform and purified by silica gel chromatography, eluting in 5-40% (10% NH₄OH/methanol) in chloroform. The desired product was collected and concentrated to give (5R*,5'R*)—N-(thiazolo[5,4-b]pyridin-2-yl)-4'H-1-azaspiro[bicyclo[3.2.1]octane-6,5'-oxazol]-2'-amine as a white solid (89 mg, 0.282 mmol, 32%). ¹H NMR (500 MHz, DMSO-d₆) δ ppm 9.18 (br. s., 1H) 8.30 (dd, J=4.58, 1.53 Hz, 1H) 7.90 (dd, J=7.93, 1.53 Hz, 1H) 7.37 (dd, J=8.09, 4.73 Hz, 1H) 3.78-3.81 (m, 1H) 3.70-3.74 (m, 1H) 3.31-3.45 (m, 1H) 3.28 (dd, J=14.34, 3.36 Hz, 1H) 3.07 (d, J=14.04 Hz, 1H) 2.80-2.95 (m, 3H) 2.72-2.81 (m, 1H) 2.05-2.21 (m, 2H) 1.65-1.88 (m, 2H). LC/MS RT=0.608 mins [M+H]=315.99.

EXAMPLES 5a, 5b

The title compound was separated into individual enantiomers by super critical fluid chromatography. The separation was run on a Chiralpak AS-H column with a mobile phase of 30% MeOH with 0.1% DEA in CO2. Peak 1 eluted at 3.76 mins and peak 2 came out at 6.27 mins.

EXAMPLE 5a

Peak 1: 1H NMR (400 MHz, DMSO-d₆) δ ppm 9.12 (1H, br. s.), 8.24-8.38 (1H, m), 7.91 (1H, dd, J=8.16, 1.38 Hz), 7.38 (1H, dd, J=8.03, 4.77 Hz), 3.78-3.85 (1H, m), 3.69-3.78 (1H, m), 3.27 (1H, d, J=3.26 Hz), 3.08 (1H, d, J=14.31 Hz), 2.73-2.96 (4H, m), 2.08-2.21 (2H, m), 1.70-1.90 (2H, m), 1.40 (1H, d, J=13.30 Hz). LC/MS R.T.=0.58 mins (M+H=315.95

EXAMPLE 5b

Peak 2: 1H NMR (400 MHz, DMSO-d₆) δ ppm 9.11 (1H, br. s.), 8.18-8.37 (1H, m), 7.91 (1H, dd, J=8.03, 1.51 Hz), 7.38 (1H, dd, J=8.03, 4.77 Hz), 3.77-3.85 (1H, m), 3.69-3.77 (1H, m), 3.29 (1H, dd, J=14.31, 126 Hz), 3.08 (1H, d, J=14.31 Hz), 2.74-2.96 (4H, m), 2.04-2.22 (2H, m), 1.69-1.90 (2H, m), 1.39 (1H, d, J=14.05 Hz). LC/MS R.T.=1.078 mins (M+H=316.09)

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

The invention claimed is:
1. A compound of formula I, or a stereoisomer thereof,

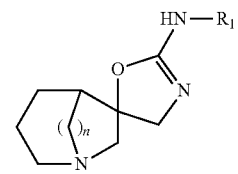

wherein
  $R^1$ is selected from the group consisting of $R^1$ is selected from the group consisting of benzothiazolyl, methoxybenzothiazolyl, thiazolopyridinyl, and isoquinoinyl;
  and
  n is 1;
or a pharmaceutically acceptable salt thereof.
2. A compound of claim 1 selected from the group consisting of (5S*,5'R*)—N-(benzo[d]thiazol-2-yl)-4'H-1-azaspiro[bicyclo[3.2.1]octane-6,5'-oxazol]-2'-amine, (5S*,5'R*)—N-(6-methoxybenzo[d]thiazol-2-yl)-4'H-1-azaspiro[bicyclo[3.2.1]octane-6,5'-oxazol]-2'-amine, (5S*5'R*)—N-(thiazolo[5,4-b]pyridin-2-yl)-4'H-1-azaspiro[bicyclo[3.2.1]

octane-6,5'-oxazol]-2'-amine, (5S*,5'R*)—N-(isoquinolin-3-yl)-4'H-1-azaspiro[bicyclo[3.2.1]octane-6,5'-oxazol]-2'-amine, (5R*,5'R*)—N-(thiazolo[5,4-b]pyridin-2-yl)-4'H-1-azaspiro[bicyclo[3.2.1]octane-6,5'-oxazol]-2'-amine; or a pharmaceutically acceptable salt thereof.

3. A pharmaceutical composition comprising a therapeutically effective amount of a compound of claim 1, or a pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO. : 8,507,516 B2
APPLICATION NO. : 12/911882
DATED : August 13, 2013
INVENTOR(S) : Ivar M. McDonald et al.

Page 1 of 1

It is certified that error appears in the above-identified patent and that said Letters Patent is hereby corrected as shown below:

In the Specification:

Column 7, line 64, change "isoquinoinyl," to -- isoquinolinyl, --.

In the Claims:

Claim 1:

Column 24, line 58, change "isoquinoinyl;" to -- isoquinolinyl; --.

Claim 2:

Column 24, line 66, change "(5S*5'R*)" to -- (5S*,5'R*) --.

Signed and Sealed this
Twenty-ninth Day of April, 2014

Michelle K. Lee
*Deputy Director of the United States Patent and Trademark Office*